United States Patent [19]

Sinclair et al.

[11] Patent Number: 5,252,642
[45] Date of Patent: Oct. 12, 1993

[54] DEGRADABLE IMPACT MODIFIED POLYACTIC ACID

[75] Inventors: Richard G. Sinclair, Columbus; Joseph Preston, Radnor, both of Ohio

[73] Assignee: BioPak Technology, Ltd., Golden, Colo.

[21] Appl. No.: 579,460

[22] Filed: Sep. 6, 1990

Related U.S. Application Data

[63] Continuation-in-part of Ser. No. 386,744, Jul. 31, 1989, abandoned, which is a continuation-in-part of Ser. No. 317,391, Mar. 1, 1989, abandoned.

[51] Int. Cl.$^5$ .................. C08L 7/00; C08L 9/00; C08L 67/02; C08L 67/04
[52] U.S. Cl. .................. 524/108; 524/310; 524/320; 525/92; 525/186; 525/190; 525/332.9; 525/333.1; 525/386; 525/411; 525/415; 525/437; 525/450; 525/454; 525/938
[58] Field of Search ............ 525/185, 186, 411, 415, 525/437, 450, 938, 190, 454, 332.9, 333.1, 386, 92; 524/108, 310, 320

[56] References Cited

U.S. PATENT DOCUMENTS

| | | | |
|---|---|---|---|
| 1,995,970 | 3/1935 | Dorough | 260/2 |
| 3,565,869 | 2/1971 | DeProspero | 260/78.3 |
| 3,636,956 | 1/1972 | Schneider | 128/335.5 |
| 3,755,558 | 8/1973 | Schribner | 424/47 |
| 3,982,543 | 9/1976 | Schmitt et al. | 128/335.5 |
| 4,279,249 | 7/1981 | Vert et al. | 128/92 D |
| 4,526,938 | 7/1985 | Churchill et al. | 525/415 |
| 4,534,349 | 8/1985 | Barrows | 128/334 R |
| 4,603,171 | 7/1986 | Hsieh | 525/205 |
| 4,621,638 | 11/1986 | Silvestrini | 128/335.5 |
| 4,646,741 | 3/1987 | Smith | 128/334 R |
| 4,661,530 | 4/1987 | Gogolewski et al. | 521/137 |
| 4,719,246 | 1/1988 | Murdoch et al. | 521/134 |
| 4,720,384 | 1/1988 | DeLuccio et al. | 424/78 |
| 4,741,337 | 3/1988 | Smith et al. | 128/334 R |
| 5,076,983 | 12/1991 | Lommis et al. | 264/101 |

FOREIGN PATENT DOCUMENTS

| | | |
|---|---|---|
| 58481 | 8/1982 | European Pat. Off. . |
| 281482 | 7/1988 | European Pat. Off. . |
| 311065 | 12/1989 | European Pat. Off. . |
| 9001521 | 2/1900 | PCT Int'l Appl. . |
| 84/00303 | 2/1984 | PCT Int'l Appl. . |
| 86/00533 | 1/1986 | PCT Int'l Appl. . |
| 87/00419 | 1/1987 | PCT Int'l Appl. . |

OTHER PUBLICATIONS

Biodegradable Materials of Poly(L-lactic acid): Melt-spun and Solution-spun Fibres; Eling, B. et al; Polymer, vol. 23, Oct. 1982, pp. 1587-1593.

Porous Biomedical Materials Basedon Mixures of Polyactides and Polyurethanes, Gogolewski S., et al; Makromol. Chem. Rapid Commun., 3, 1982, pp. 839-845.

Microporous, complaint, biodegradable vascular grafts for the regeneration of the arterial wall in rat abdominal aorta; Van der Lei, B. et al; Surgery, 98, 1985, pp. 955-962.

Biodegradable PEO/PLA block copolymers; Cohnm, Daniel et al; Journal of Biomedical Materials Research, vol. 22, pp. 993-1009 (1988).

Phase Separation of Poly(Ethylene Glycol)/Poly(Lactic Acid) Blends; Younes, H. et al; Eur. Polym. J. of vol. 24, No. 8, 1988, pp. 765-773.

Survey of Polymer Blends Containing Poly(3-Hydroxybutrate-co-16% Hydroxyvalerate); Dave, P. B. et al; Polymer Preprints, vol. 31, No. 1, Apr. 1990, pp. 442-443.

Novel Poly(d,l-Lactic Acid)-Ethylene/Vinyl Acetate Blends for Controlled Release Applications; Dollinger, H. M. et al; Polymer Preprints, vol. 31, No. 1, Apr. 1990, pp. 429-430.

*Primary Examiner*—Patricia A. Short
*Attorney, Agent, or Firm*—Sheridan Ross & McIntosh

[57] ABSTRACT

An environmentally degradable composition comprises blends of a physical mixture of a poly(lactic acid), comprising about 1 to 99 weight percent of the composition, and an elastomeric blend compatible polymer, such as a segmented polyester, that provides improved impact resistance to the poly(lactic acid) and is discrete and intimately bound; plasticizer is added to the blend that is selected from the group consisting of lactide monomer, lactic acid oligomer, lactic acid, and mixtures thereof. Other plasticizer that may be added includes one or more derivatives of an oligomer of lactic acid, its esters and copolymer.

31 Claims, No Drawings

DEGRADABLE IMPACT MODIFIED POLYACTIC ACID

This application is a continuation-in-part of Ser. No. 07/386,844 filed Jul. 31, 1989, now abandoned, which is a continuation-in-part of Ser. No. 07/317,391 filed Mar. 1, 1989, now abandoned.

FIELD OF THE INVENTION

The invention relates to the blending of compatible elastomers with polylactides. This provides impact-resistant modified poly(lactic acids) that are useful in a wide variety of applications including those where impact-modified polystyrene would be used.

The invention further relates to a method for producing packaging items and to the unique product thereof. The invention has utility in making a product that has the characteristics of the usual impact-resistant plastics yet is environmentally degradable.

The present application is related to the application entitled BIODEGRADABLE PACKAGING THERMOPLASTICS FROM POLYLACTIC ACID having attorney docket number PF 2767-2, and the application entitled BIODEGRADABLE REPLACEMENT OF CRYSTAL POLYSTYRENE having attorney docket number PF 2771-2, and the application entitled BLENDS OF POLYLACTIC ACID, having attorney docket number PF 2772-2, all having the same assignee and filing date as the present application, the disclosures of which are incorporated by reference herein.

BACKGROUND OF THE INVENTION

There is a need for an environmentally degradable packaging thermoplastic as an answer to the tremendous amounts of discarded plastic packaging materials. U.S. plastic sales in 1987 were 53.7 billion lbs of which 12.7 billion lbs were listed as plastics in packaging. A significant amount of this plastic is discarded and becomes a plastic pollutant that is a blot on the landscape and a threat to marine life. Mortality estimates range as high as 1-2 million seabirds and 100,000 marine mammals per year.

A further problem with the disposal of plastic packaging is the concern for dwindling landfill space. It has been estimated that most major cities will have used up available landfills for solid waste disposal by the early 1990's. Plastics comprise approximately 3 percent by weight and 6 percent volume of solid waste.

One other disadvantage of conventional plastics is that they are ultimately derived from petroleum, which leaves plastics dependent on the uncertainties of foreign crude oil imports. A better feedstock would be one that partially derives from renewable, domestic resources thus reducing reliance on imports.

However, there are good reasons for the use of packaging plastics. They provide appealing aesthetic qualities in the form of attractive packages which can be quickly fabricated and filled with specified units of products. The packages maintain cleanliness, storage stability, and other desirable qualities such as transparency for inspection of contents. These packages are known for their low cost of production and chemical stability. This stability, however leads to very long-life of the plastic, so that when its one-time use is completed, discarded packages remain on, and in, the environment for incalculably long times.

There are many citations in the prior art for the preparation of lactic acid polymers and copolymers. The earliest processes used lactic acid directly as the monomer, cf., e.g., U.S. Pat. Nos. 1,995,970; 2,362,511; and 2,683,136. The poly(lactic acids) of these patents were of low molecular weights, tacky and without good physical properties. U.S. Pat. No. 2,668,162 (Lowe, DuPont) discloses the use of lactide as the monomer. Lactide is the dilactone, or cyclic dimer, of lactic acid. When lactide is formed, by-product water is eliminated, permitting the lactide subsequently to be ring-opened polymerized to linear polyester of high molecular weight without tedious condensation methods. Polymers and copolymers of excellent physical properties were obtained by using the intermediate, lactide, to form poly(lactic acid). Copolymers of lactide and glycolide are disclosed by the Lowe patent which are tough, clear, cold-drawable, stretchable, and capable of forming at 210 C into self-supporting films.

Other patents related to forming lactide polymers include U.S. Pat. Nos. 2,703,316; 2,758,987; 2,951,828; 3,297,033; 3,463,158; 3,531,561; 3,636,956; 3,736,646; 3,739,773; 3,773,919; 3,887,699; 3,797,499; 4,273,920; 4,471,077; and 4,578,384; German Offenlegungsschrift 2,118,127; Canadian Patents 808,731; 863,673; and 923,245.

U.S. Pat. No. 4,661,530, discloses the mixtures of a poly(L-lactic acid) and/or poly(D,L-lactic acid) and segmented polyester urethanes or polyether urethanes. Biodegradable materials are formed that are useful in synthetic replacements of biological tissues and organs in reconstructive surgery. Porous structures are formed together with elastic fibers.

PCT publication WO 87/00419 to Barrows reveals a bone spacer comprising a blend or mixture of a nonabsorbable polymer and a bioabsorbable polymer, polylactic acid is one of the preferred biodegradable polymers but plasticizers are not revealed therein. PCT publication WO 84/00303 to Gogolewski et al suggests blends of polyesters and polyurethanes for preparing surgical filaments. Cohn et al, in Biodegradable PEO/PLA Block Copolymers, Journal of Biomed. Mater. Res., Vol. 22, p. 993, 1988, reveals a physical mixture of poly(ethylene oxide) and poly(lactic acid).

BRIEF DESCRIPTION OF THE INVENTION

An environmentally degradable composition is disclosed comprising blends of a physical mixture of poly(lactic acid) and blend-compatible elastomers that provide improved impact resistance to the blended composition. Such an elastomer may be, for example, a Hytrel TM, a segmented polyester which is a block copolymer of hard crystalline segments of poly(butylene terephthalate) and soft long chain segments of polyether glycol). One example is known by the trade name as Hytrel TM 4056 (DuPont) segmented polyester.

In addition to the above there are disclosed blends including one or more plasticizers. The blends are useful with the above materials as well as with others as further discussed herein. The poly(lactic acid) present in the blends may be represented by the structure:

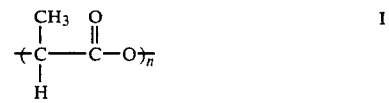

where n is an integer between 75 and 10,000.

Plasticizers useful with the invention include D-lactic acid, L-lactic acid, racemic D,L-lactic acid, D-lactide, L-lactide, meso D,L-lactide, racemic D,L-lactide, oligomers of lactic acid, oligomers of lactide, and mixtures thereof. The oligomers of lactic acid, and oligomers of lactide are defined by the formula:

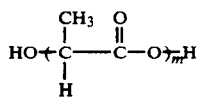     II where m is an integer: $2<m<75$. These limits correspond to number average molecular weights below about 5,400 and below about 720 respectively.

Further plasticizers useful in the invention include oligomeric derivatives of lactic acid, selected from the group defined by the formula:

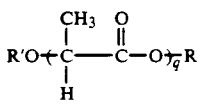     III where R=H, alkyl, aryl, alkylaryl or acetyl, and R is saturated, where R'=H, alkyl, aryl, alkylaryl or acetyl, and $R^1$ is saturated, where R and R' cannot both be H, where q is an integer: $2<q<75$, and mixtures thereof.

The plasticizers may be present in any amount that provides the desired characteristics. For example, the various types of plasticizers discussed herein and in the copending applications provide for (a) more effective compatibilization of the melt blend components; (b) improved processing characteristics during the blending and processing steps; and (c) control and regulate the sensitivity and degradation of the polymer by moisture. For pliability, plasticizer is present in higher amounts while other characteristics are enhanced by lower amounts. The compositions allow many of the desirable characteristics of pure nondegradable polymers. In addition, the presence of plasticizer facilitates melt processing, prevents discoloration, and enhances the degradation rate of the compositions in contact with the environment. The intimately plasticized composition should be processed into a final product in a manner adapted to retain the plasticizer as an intimate dispersion in the polylactic acid and/or its coblended polymer for certain properties. These steps can include: (1) quenching the composition at a rate adapted to retain the plasticizer as an intimate dispersion; (2) melt processing and quenching the composition at a rate adapted to retain the plasticizer as an intimate dispersion; and (3) processing the composition into a final product in a manner adapted to maintain the plasticizer as an intimate dispersion.

Particularly advantageous is the sequential incorporation of plasticizer into poly(lactic acid) and the other polymer by melt blending with them, a first plasticizer selected from the group consisting of oligomers of lactic acid, oligomers of lactide, and mixtures thereof; and melt blending with the blend a second plasticizer selected from the group consisting of lactic acid, L-lactide, D-lactide, meso D,L-lactide, racemic D,L-lactide, and mixtures thereof. If desired, a first plasticizer defined by the formula III may be used alone or in admixture with an oligomer of formula II. This procedure allows the blending of the first plasticizer at a first temperature and the blending of the second plasticizer at a second temperature lower than the first temperature.

DETAILED DESCRIPTION OF THE INVENTION AND PREFERRED EMBODIMENTS

Within the scope of the invention is included those impact modifiers which are elastomeric discrete, intimately bound and the polylactic (or polylactide)/impact modifier blend is hydrophobic, nonporous, nonswellable in water, and hydrolyzes at the same rate or slower than the poly(lactic acid) (or polylactide) alone; and melt compatible with poly(lactic acid). By "melt compatible", it is meant all those polymers which can be intimately mixed with poly(lactic acid) as discussed in our copending application "Blends of Polylactic Acid". The mix would result in a substantially homogeneous blend. All of the examples herein exhibit these properties. Since both lactic acid and lactide can achieve the same repeating unit, the general term poly(lactic acid) as used herein refers to polymers having the repeating unit of formula I without any limitation as to how the polymer was made (e.g. from lactides, lactic acid, or oligomers), and without reference to the degree of polymerization or level of plasticization.

The environmentally degradable compositions disclosed herein are at least partially degradable. That is the poly(lactic acid) portion of the composition will decompose relatively rapidly compared to the more stable portions of the blend and cause a physical deterioration of the blended material. For example, when the compositions are intimate and homogeneous blends with small domain sizes the physical deterioration will destroy the original formed product. The compositions herein provide environmentally acceptable materials because their physical deterioration and degradation is much more rapid than conventional nondegradable plastics. Further, since a major portion of the composition will be poly(lactic acid), and/or a lactic acid derived lactide or oligomer only a small portion of more slowly degrading elastomer residue will remain (e.g. segmented polyester). This residue will have a high surface area and is expected to decompose faster than a bulk formed product.

The examples below show the blending of poly(lactic acid) (PLA) with a Hytrel ™, a segmented polyester which is a block copolymer of hard crystalline segments of poly(butylene terephthalate) and soft long-chain segments of polyether glycol). It is shown that poly(lactic acid) is melt compatible with this elastomer and the effect on its physical properties.

D-lactide is a dilactide, or cyclic dimer, of D-lactic acid. Similarly, L-lactide is a cyclic dimer of L-lactic acid. Meso D,L-lactide is a cyclic dimer of D- and L-lactic acid. Racemic D,L-lactide comprises a 50/50 mixture of D-, and L-lactide. When used alone herein, the term "D,L-lactide" is intended to include meso D,L-lactide or racemic D,L-lactide. Poly(lactic acid) may be prepared from one or more of the above.

EXAMPLE 1

A polylactide copolymer without Hytrel ™ segmented polyester was prepared using the procedure from Example 1 of copending application Ser. No. 229,939 and tested for Izod impact strength. Results are shown in the Table. For further comparison, Table 1 of Ser. No. 229,939 lists the Izod impact strength of other ratios of L-lactide to D-L lactide.

EXAMPLE 2

Into a 3-neck, 250 ml, round-bottom flask is weighed 10.96 g of D,L-lactide, 108.86 g of L-lactide, and 5.27 g of Hytrel TM 4056 segmented polyester (Du Pont, a thermoplastic elastomer). Hytrel TM 4056 segmented polyester is a polyester elastomer with a Shore D durometer, low flexural modulus, high melt viscosity, a melt index of 7, a sp. gr. of 1.17, a m.p. 334 F, a vicat softening temperature of 234 F, and an extrusion temperature of 340 F-400 F. The flask is fitted with a mechanical stirrer and a nitrogen inlet and outlet. The contents are heated by means of an oil bath. The Hytrel TM segmented polyester dissolves in the molten lactides at 170 C. A catalyst solution is prepared by dissolving 10 ml of stannous octoate in 60 ml of toluene and distilling 10 ml into the toluene. A 100 microliter portion of the catalyst solution is injected into the solution of lactide and Hytrel TM segmented polyester. The mixture is stirred under nitrogen at 155 C for approximately 64 hours.

The viscosity increases sharply and the mixture turns cloudy. The product is tough and opaque. Films of 8-9 mil thickness were compression molded at 155 C and the tensile properties measured, as shown in the Table.

Slabs, ⅛ inch thick, were compression molded and their Izod impact strength measured using a 2 pound pendulum. The results are recorded in the Table where the data are compared to a similar polylactide copolymer of Example 1 without Hytrel TM segmented polyester, and to data for so-called medium-impact polystyrene, Example 7.

EXAMPLE 3

800.0 g of L-lactide and 202.3 g of racemic D,L-lactide are copolymerized using 1.0 ml of the catalyst solution by methods similar to Example 2, omitting the Hytrel TM segmented polyester. The lactide copolymer is clear and colorless. In a separate polymerization 104.0 g of L-lactide is melt polymerized using 100 microliters of catalyst. The polymer poly(L-lactic acid), is white, crystalline, and crazes easily when struck.

An electrically-heated, 2-roll mill is heated to 375 F, then 8.4 g of Hytrel TM segmented polyester and 19.2 g of poly(L-lactic acid) are banded on the roll. To this was added 172.4 of the lactide copolymer. The mixture blends easily and is removed from the rolls, molded, and tested as in Example 2. The data are recorded in the Table.

EXAMPLE 4

The lactide copolymer of Example 3, 80 g, the poly(L-lactic acid) of Example 3, 10 g, and 10 g of Hytrel TM 4056 segmented polyester are 2-roll, mill-blended as described previously in Example 3. The blend was tested as before and the data are recorded in the Table.

EXAMPLE 5

100 g of the blend of Example 3 was further blended with 20 g of Hytrel TM 4056 segmented polyester. The mixture easily mixed on the roll and was apparently quite compatible. The physical properties were measured as described previously and recorded in the Table.

EXAMPLES 6 AND 7

Typical crystal polystyrene and medium-impact polystyrene were tested and used for comparative controls.

The above results clearly indicate that polylactides can be impact-modified. The blends provided significantly higher Izod impact strengths than the crystal polystyrene control and gave slightly lower or equivalent impact strengths compared to medium-impact polystyrene. Those skilled in the art will recognize that the data on impact-strength in the Table can be improved further by optimizing the amount and type of impact modifier.

Since polylactides have been shown previously in copending application, "BLENDS OF POLYLACTIC ACID" to be blend-compatible with numerous other compounds and thermoplastics, the process of impact-modifying polylactides is generic to mixtures of polylactides and elastomers that are blend-compatible. Also, those skilled in the art will recognize that the data of the Table will improve as the blends are injection-molded, as opposed to compression-molded, since the former often induces orientation of the specimens and, consequently, a profound improvement in impact strength.

TABLE

| | PHYSICAL PROPERTY COMPARISONS OF IMPACT-MODIFIED POLYACTIDES | | | | | | |
|---|---|---|---|---|---|---|---|
| | Composition, weight percent | | | Tensile | | Tangent | Izod Impact |
| Example No. | Lactide Copolymer | L-lactide Homopolymer | Hytrel TM (a) | Strength, psi(b,c) | Elongation, percent | Modulus, psi | Strength ft-lb/in.(c) |
| 1 | 80(d) | 20 | 0 | 7,667 | 3.4 | 322,679 | 0.3-0.4 |
| 2 | 95.8(e) | 0 | 4.2(f) | 8,636 | 3.1 | 359,409 | 0.40 |
| 3 | 86.2(g) | 9.6 | 4.2(h) | 7,823 | 3.1 | 346,502 | 0.51 |
| 4 | 80.0(g) | 10.0 | 10.0(h) | — | — | — | 0.53 |
| 5 | 71.2(g) | 7.9 | 20.9(h) | — | — | — | 0.61 |
| 6(i) | 0 | 0 | 0 | 6,118 | 3.2 | 267,245 | 0.18 |
| 7(j) | 0 | 0 | 0 | 6,090 | 4 | — | 0.7 |

(a)DuPont Hydtrel TM 4056, a thermoplastic polyester elastomer.
(b)ASTM D 882,7-15 mil film thickness.
(c)Compression-molded specimens.
(d)control, 90/10, L-D/L-lactide copolymer.
(e)91/9, L-D/L-lactide copolymer.
(f)Hytrel TM dissolved in lactide monomers before 170 C. polymerization.
(g)80/20, L-D/L-lactide copolymer.
(h)2-Roll mill-blend at 185-190 C.
(i)Control, crystal polystyrene, melt-index 1.7.
(j)Control, medium-impact polystyrene The compositions are useful thermoplastics that can be melt fabricated by conventional processes such as extrusion and molding.

The blends preferably use a physical mixture of poly(lactic acid) of the structure

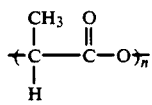

(I)

where n is an integer between 75 and 10,000; and a polymer comprising a segmented polyester. The poly(lactic acid) content may vary over a wide latitude such as between about 1 and about 99 weight percent. A useful composition is that where the poly(lactic acid) comprises 50 to 99 weight percent of the composition. A preferred composition has a poly(lactic acid) content of 70 to 80 weight percent, while other useful compositions include about 5 to about 20 weight percent, depending on the final use of the composition.

Two embodiments of the general process for producing the composition include (1) melt blending of poly(lactic acid) with a blend compatible polymer that provides improved impact resistance and is discrete and intimately bound (such as a segmented polyester); and (2) solution blending during poly(lactic acid) polymerization as in Example 2 where Hytrel TM segmented polyester is dissolved in the poly(lactic acid). The poly(lactic acid) provided preferably has the formula I. If desired, plasticizer in pliable forming amounts may be added to the blend that is selected from the group consisting of lactide monomer, lactic acid oligomer, lactic acid, and mixtures thereof. The oligomers are defined by the formula:

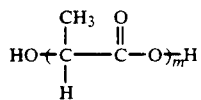

(II)

where m is an integer: $2 \leq m \leq 75$, and is preferably $2 < m < 10$. Other plasticizer that may be added include one or more derivatives of an oligomer of lactic acid defined by the formula:

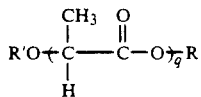

(III)

where R = H, alkyl, aryl, alkylaryl or acetyl, and R is saturated, where R' = H, alkyl, aryl, alkylaryl or acetyl, and R' is saturated, where R and R' cannot both be H, and where q is an integer: $2 \leq q \leq 75$, and is preferably. Preferably q is an integer: $2 \leq q \leq 10$. Addition of plasticizer will provide additional unique physical properties and processing advantages as discussed in the referenced copending applications.

The plasticizers may be present in any amount that provides the desired characteristics. For example, the various types of plasticizers discussed herein and in the copending applications provide for (a) more effective compatibilization of the melt blend components so that greater intimacy is achieved; (b) improved processing characteristics during the blending and processing steps; and (c) control and regulate the sensitivity and degradation of the polymer by moisture. For pliability, plasticizer is present in higher amounts while other characteristics such as stiffness are enhanced by lower amounts. The compositions allow many of the desirable characteristics of pure nondegradable polymers. In addition, the presence of plasticizer facilitates melt processing, prevents discoloration, and enhances the degradation rate of the compositions in contact with the environment. The intimately plasticized composition should be processed into a final product in a manner adapted to retain the plasticizer as an intimate dispersion in the polylactic acid and/or its coblended polymer for certain properties. These steps can include: (1) quenching the composition at a rate adapted to retain the plasticizer as an intimate dispersion; (2) melt processing and quenching the composition at a rate adapted to retain the plasticizer as an intimate dispersion; and (3) processing the composition into a final product in a manner adapted to maintain the plasticizer as an intimate dispersion. The plasticizers are preferably at least intimately dispersed within the polylactic acid if not in the co-blended polymer.

Microscopic examination of the Hytrel TM segmented polyester/poly(lactic acid) mixture revealed that the dispersed Hytrel TM segmented polyester is present in small spherical domains a few microns or less in size. These domain sizes can be adjusted by the mixing conditions such as time, speed of mixing, and temperature.

Therefore, for example, the polymer, or polymers, added to the poly(lactic acid), should be generally of small, heterogeneous domain size, less than 10 microns, and can be submicroscopic, or dissolved, in the poly(lactic acid). In addition, this impact modifier must be elastomeric.

While not wishing to be held to any particular theory, it is believed that the present invention provides a continuous matrix of poly(lactic acid) containing intimately mixed microscopic domains of Hytrel TM segmented polyester that act as crack arrestors since the latter is a thermoplastic elastomer compatible with poly(lactic acid).

For this purpose, the impact modifier must be elastomeric and intimately bound into the poly(lactic acid) as a discrete heterogeneous phase. The added polymer, the impact modifier, can be a thermoplastic elastomer, or a crosslinked rubber, to achieve this elastic behavior. Examples are natural rubber and styrene-butadiene copolymers.

Further examples of impact modifiers useful in the invention include polyisoprene (gutta percha), styrene-isoprene-styrene block copolymers, acrylonitrile-butadiene-styrene block copolymers, styrene-ethylene-styrene block copolymers, propylene-ethylene-propylene block copolymers, propylene-isoprene-propylene block copolymers, mixtures thereof, and the like. Polyurethanes that are not significantly water swellable or water soluble may also be used.

In a test of material placed in water for five months, the material embrittled compared to a material not exposed to water. In addition the water turned acidic indicating breakdown of poly(lactic acid) to lactic acid. It was further apparent that poly(lactic acid) alone degraded faster than the Hytrel TM segmented polyester/poly(lactic acid) mixture. Thus Hytrel TM segmented polyester can also be used to retard the degradation rate of poly(lactic acid).

A third component can be added which is compatible with the other components discussed above to achieve improved compatibility. Thus, where the poly(lactic acid) and the impact modifier have poor compatibility, a third component can be added to improve the compatibility. This third component is usually added where it is compatible with the other two, individually, and where the other two, poly(lactic acid) and impact modifier are not very compatible. This works by increasing the interfacial bonding between poly(lactic acid) and elastomeric impact modifier. However, what is surprising is the wide latitude of compatibility of poly(lactic acid) with other polymer types, both polar and nonpolar. This can be referred to in the above cited copending application.

If desired, minor amounts of plasticizer such as glycolide, poly(glycolic acid), caprolactone, and valerolactone may be added.

The compositions herein can be processed by melt fabrication into useful articles of manufacture such as containers, eating utensils, trays, plates, drinking cups, single serving trays, syringes, medical trays, and the like. The compositions are especially useful for articles having only a one time use or a short life span in use before disposal.

While the invention has been described above with reference to various specific examples and embodiments, it will be understood that the invention is not limited to such illustrated examples and embodiments and may be variously practiced within the scope of the claims hereinafter made.

We claim:

1. A degradable composition comprising: blends of a physical mixture of:
   a. a poly(lactic acid); and
   b. a blend compatible polymer that provides improved impact resistance to the poly(lactic acid), wherein the polymer is selected from the group consisting of a block copolymer of hard crystalline segments of poly(butylene terephthalate) and soft long chain segments of poly(ether glycols), natural rubber, styrene-butadiene copolymers, and mixtures thereof; and
   wherein said poly(lactic acid) and said blend compatible polymer are present as discrete heterogeneous phases.

2. The composition of claim 1, wherein the blend compatible polymer is a Hytrel TM.

3. The composition of claim 1, wherein the Hytrel TM is a Hytrel TM 4056.

4. A process for producing the composition of claim 1, comprising:
   a. providing a poly(lactic acid);
   b. selecting a blend compatible polymer that provides improved impact resistance to the poly(lactic acid) from the group consisting of a block copolymer of hard crystalline segments of poly(butylene terephthalate) and soft long chain segments of polyether glycols), natural rubber, styrene-butadiene copolymers, and mixtures thereof; and
   c. blending the polymers of steps a and b.

5. The process of claim 4, whereby Hytrel TM is selected.

6. The process of claim 5, whereby Hytrel TM 4056 is selected.

7. A process for producing the composition of claim 1, comprising:
   a. mixing one or more lactides selected from the group consisting of D-lactide, L-lactide, meso D,L-lactide, racemic D,L-lactide and mixtures thereof with a blend compatible polymer that provides improved impact resistance to the composition, wherein the blend compatible polymer is selected from the group consisting of a block copolymer of hard crystalline segments of poly(butylene terephthalate) and soft long chain segments of poly(ether glycols), natural rubber, styrene-butadiene copolymers, and mixtures thereof;
   b. heating and dissolving the blend compatible polymer in the lactide(s) of step a to form a solution; and
   c. polymerizing the lactide(s) in the solution.

8. The process claim 7, wherein the selected blend compatible polymer is a Hytrel TM.

9. The process claim 8, wherein the selected Hytrel TM is Hytrel TM 4056.

10. An environmentally degradable composition comprising blends of a physical mixture of:
    a) a poly(lactic acid) having a number average molecular weight greater than about 5,400;
    b) an elastomeric blend compatible polymer that provides an improved impact resistant composition, and the elastomeric blend compatible polymer is intimately bound into the poly(lactic acid) as a discrete heterogeneous phase; and
    c) a plasticizer selected from the group consisting of lactic acid, D-lactide, L-lactide, meso D,L-lactide, racemic D,L-lactide, oligomers of lactic acid, oligomers of lactide, and mixtures thereof, wherein the oligomers have a number average molecular weight below about 5,400, and wherein the plasticizer is intimately dispersed within at least the poly(lactic acid);
    wherein the elastomeric blend compatible polymer is selected from the group consisting of polyisoprene (gutta percha), styrene-isoprene-styrene block copolymers, acrylonitrile-butadiene-styrene block copolymers, styrene-ethylene-styrene block copolymers, propylene-ethylene-propylene block copolymers, propylene-isoprene-propylene block copolymers and mixtures thereof.

11. An environmentally degradable composition comprising blends of a physical mixture of:
    a) a poly(lactic acid) having a number average molecular weight greater than about 5,400;
    b) an elastomeric blend compatible polymer that provides an improved impact resistant composition, and the elastomeric blend compatible polymer is intimately bound into the poly(lactic acid) as a discrete heterogeneous phase; and
    c) a plasticizer selected from the group consisting of lactic acid, D-lactide, L-lactide, meso D,L-lactide, racemic D,L-lactide, oligomers of lactic acid, oligomers of lactide, and mixtures thereof, wherein the oligomers have a number average molecular weight below about 5,400, and wherein the plasticizer is intimately dispersed within at least the poly(lactic acid);
    wherein the elastomer blend compatible polymer is selected from polyurethanes that are not significantly water swellable or water soluble.

12. An environmentally degradable composition, comprising blends of a physical mixture of:
    a) a poly(lactic acid) having a number average molecular weight greater than about 5,400;
    b) an elastomeric blend compatible polymer that provides an improved impact resistant composition, and the elastomeric blend compatible polymer is intimately bound into the poly(lactic acid) as a discrete heterogeneous phase; and
    c) a plasticizer selected from the group consisting of lactic acid, D-lactide, L-lactide, meso D,L-lactide, racemic D,L-lactide, oligomers of lactic acid, oligomers of lactide, and mixtures thereof, wherein the oligomers have a number average molecular weight below about 5,400, and wherein the plasticizer is intimately dispersed within at least the poly(lactic acid);

wherein the elastomeric blend compatible polymer is a block copolymer of hard crystalline segments of poly(butylene terephthalate) and soft long chain segments of poly(ether glycol).

13. The composition of claim 12, wherein the blend compatible polymer is a Hytrel ™ 4056 segmented polyester.

14. A process for producing an environmentally degradable composition, comprising:
 a. providing a poly(lactic acid) having a number average molecular weight greater than about 5,400;
 b. providing a plasticizer selected from the group consisting of lactic acid, D-lactide, L-lactide, meso D,L-lactide, racemic D,L-lactide, and mixtures thereof;
 c. providing an elastomeric blend compatible polymer that provides an improved impact resistant composition in which the elastomeric blend compatible polymer is intimately bound into the poly(lactic acid) as a discrete heterogenous phase; and
 d. blending the polymers of steps (a) and (c) with the plasticizer of step (b);

wherein the elastomeric blend compatible polymer is selected from the group consisting of polyisoprene (gutta percha), styrene-isoprene-styrene block copolymers, acrylonitrile-butadiene-styrene block copolymers, styrene-ethylene-styrene block copolymers, propylene-ethylene-propylene block copolymers, propylene-isoprene-propylene block copolymers and mixtures thereof.

15. A process for producing an environmentally degradable composition, comprising:
 a. providing a poly(lactic acid) having a number average molecular eight greater than about 5,400;
 b. providing a plasticizer selected from the group consisting of lactic acid, D-lactide, L-lactide, meso D,L-lactide, racemic D,L-lactide, and mixtures thereof;
 c. providing an elastomeric blend compatible polymer that provides an improved impact resistant composition in which the elastomeric blend compatible polymer is intimately bound into the poly(lactic acid) as a discrete heterogenous phase; and
 d. blending the polymers of steps (a) and (c) with the plasticizer of step (b);

wherein the elastomeric blend compatible polymer is selected from polyurethanes that are not significantly water swellable or water soluble.

16. A process for producing an environmentally degradable composition, comprising:
 a. providing a poly(lactic acid) having a number average molecular weight greater than about 5,400;
 b. providing a plasticizer selected from the group consisting of lactic acid, D-lactide, L-lactide, meso D,L-lactide, racemic D,L-lactide, and mixtures thereof;
 c. providing an elastomeric blend compatible polymer that provides an improved impact resistant composition in which the elastomeric blend compatible polymer is intimately bound into the poly(lactic acid) as a discrete heterogenous phase, said elastomeric blend compatible polymer is selected from the group consisting of a block copolymer of hard crystalline segments of poly(butylene terephthalate) and soft long chain segments of poly(ether glycols), natural rubber, styrene-butadiene copolymers, and mixtures thereof; and
 d. blending the polymers of steps (a) and (c) with the plasticizer of step (b).

17. The process of claim 16, wherein Hytrel ™ 4056 segmented polyester is selected.

18. A process for producing an environmentally degradable composition, comprising:
 a. mixing one or more lactides selected from the group consisting of D-lactide, L-lactide, meso D,L-lactide, racemic D,L-lactide and mixtures thereof with an elastomeric blend compatible polymer that provides an improved impact resistant composition in which the elastomeric blend compatible polymer is intimately bound into the poly(lactic acid) as a discrete heterogenous phase, wherein the resulting composition is hydrophobic, nonporous, nonswellable in water, and hydrolyzes at the same rate or slower than the poly(lactic acid) alone;
 b. heating and dissolving the blend compatible polymer in the lactide(s) of step (a) to form a solution;
 c. polymerizing the lactide(s) in the solution to produce a poly(lactic acid) having a number average molecular weight greater than about 5,400; and
 d. incorporating into the polymerized lactides a plasticizer selected from the group consisting of lactic acid, D-lactide, L-lactide, meso D,L-lactide, racemic D,L-lactide, oligomers of lactic acid, oligomers of lactide, and mixtures thereof, wherein the oligomers have a number average molecular weight below about 5,400 and wherein the plasticizer is intimately dispersed within at least the poly(lactic acid).

19. The process of claim 18, comprising the step of fabricating the composition into useful forms by melt fabrication.

20. The process of claim 18, comprising selecting a blend compatible polymer that comprises a segmented polyester.

21. The process of claim 18, comprising selecting an elastomeric blend compatible polymer from the group consisting of polyisoprene (gutta percha), styrene-isoprene-styrene block copolymers, acrylonitrile-butadiene-styrene block copolymers, styrene-ethylene-styrene block copolymers, propylene-ethylene-propylene block copolymers, propylene-isoprene-propylene block copolymers, and mixtures thereof.

22. The process of claim 18, whereby the elastomeric blend compatible polymer is selected from polyurethanes that are not significantly water swellable or water soluble.

23. The process of claim 18, comprising selecting an elastomeric blend compatible polymer from the group consisting of a block copolymer of hard crystalline segments of poly(butylene terephthalate) and soft long chain segments of polyether glycols), natural rubber, styrene-butadiene copolymers, and mixtures thereof.

24. The process of claim 23, wherein the elastomeric blend compatible polymer comprises Hytrel ™ 56 or segmented polyester.

25. The process of claim comprising stopping the polymerization prior to completion to provide residual monomer in the composition.

26. The process of claim 18, comprising:

providing a plasticizer selected from the group consisting of one or more derivatives of an oligomer of lactic acid defined by the formula:

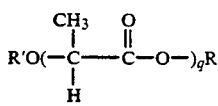

where R=H, alkyl, aryl, alkylaryl or acetyl, and R is saturated, where R'=H, alkyl, aryl, alkylaryl or acetyl, and R' is saturated, where R and R' cannot both be H, and where q is an integer: $2 \leq q \leq 75$.

27. The process of claim 18, comprising: providing:
   a. a first plasticizer selected from the group consisting of oligomers of lactic acid, oligomers of lactide, and mixtures thereof, having a number average molecular weight below about 5,400; and
   b. a second plasticizer selected from the group consisting of lactic acid, D-lactide, L-lactide, meso D,L-lactide, racemic D,L-lactide, and mixtures thereof.

28. The process of claim 27 wherein the first plasticizer is incorporated at a first temperature, and the second plasticizer is incorporated at a second temperature lower than the first temperature.

29. The process of claim 18, comprising:
   a. providing a first plasticizer selected from the group consisting of one or more derivatives of an oligomer of lactic acid defined by the formula:

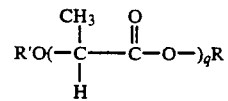

where R=H, alkyl, aryl, alkylaryl or acetyl, and R is saturated, wherein R'=H, alkyl, aryl, aklylaryl or acetyl, and R' is saturated, where R and R' cannot both be H, and where q is an integer: $2 \leq q \leq 75$; and
   b. providing a second plasticizer selected from the group consisting of lactic acid, D-lactide, L-lactide, meso D,L-lactide, racemic D,L-lactide, and mixtures thereof.

30. The process of claim 29, wherein the first plasticizer is incorporated at a first temperature, and the second plasticizer is incorporated at a second temperature lower than the first temperature.

31. The process of claim 18, in which the plasticizer is added in an amount between about 0.10 and about 10 weight percent.

* * * * *